United States Patent [19]

Miyata et al.

[11] Patent Number: 4,824,964
[45] Date of Patent: Apr. 25, 1989

[54] METHOD FOR PREPARING OPTICALLY ACTIVE N-ACETYLINDOLINE-2-CARBOXYLIC ACID

[75] Inventors: Satoru Miyata, Kariya; Hiromi Fukuda; Shinzo Imamura, both of Nagoya, all of Japan

[73] Assignee: Toray Industries, Inc., Tokyo, Japan

[21] Appl. No.: 6,312

[22] Filed: Jan. 15, 1987

Related U.S. Application Data

[63] Continuation of Ser. No. 752,900, Jul. 8, 1985, abandoned.

[30] Foreign Application Priority Data

Jul. 13, 1984 [JP]  Japan .................................. 59-144185

[51] Int. Cl.[4] ........................................... C07D 209/12
[52] U.S. Cl. ...................................... 548/490; 548/492
[58] Field of Search .................................. 548/492, 490

[56] References Cited

U.S. PATENT DOCUMENTS 4,374,847  2/1983  Gruenfeld ........................... 548/491

FOREIGN PATENT DOCUMENTS 0116468  7/1983  Japan .
0067271  4/1984  Japan .

*Primary Examiner*—David B. Springer
*Attorney, Agent, or Firm*—Austin R. Miller

[57] ABSTRACT

A resolving agent for N-acetylindoline-2-carboxylic acid, comprising an optically active α-amino-ε-caprolactam gives an optically active N-acetylindoline-2-carboxylic acid in both high yield and high optical purity.

2 Claims, No Drawings

METHOD FOR PREPARING OPTICALLY ACTIVE N-ACETYLINDOLINE-2-CARBOXYLIC ACID

This application is a continuation, of application Ser. No. 752,900, filed 7/8/85 now abandoned.

BACKGROUND OF THE INVENTION (1) Field of the Invention

This invention relates to a resolving agent for N-acetylindoline-2-carboxylic acid and a method for preparing an optically active N-acetylindoline-2-carboxylic acid.

(2) Description of the Prior Art

An optically active N-acetylindoline-2-carboxylic acid is used as the intermediate in the preparation of antihypertensive agents, for example, 1-carboxyalkanoyl-L-indoline-2-carboxylic acids. N-Acetylindoline-2-carboxylic acid obtained by chemical synthesis is the racemate and therefore it is necessary to resolve the racemate in order to obtain an optically active N-acetylindoline-2-carboxylic acid.

The prior method for preparing of an optically active N-acetylindoline-2-carboxylic acid includes the use of l-cinchonidine as the resolving agent, as shown in U.S. Pat. No. 4,374,847. The L- optical isomer of N-acetylindoline-2-carboxylic acid is especially important as the optical intermediate of antihypertensive agents, e.g., 1-carboxylalkanoyl-L-indoline-2-carboxylic acids. In the foregoing method, L-optical isomer thereof stays in the mother liquor during the optical resolution, and therefore, in order to obtain L-isomer with high optical purity, the cumbersome operations are inevitable, and it results in undesirably low yield. Additionally, natural l-cinchonidine used as the resolving agent is a relatively expensive and readily not available material on a commercial scale.

BRIEF SUMMARY OF THE INVENTION

An object of this invention is to provide a resolving agent for N-acetylindoline-2-carboxylic acid.

Another object of this invention is to provide a resolving agent for N-acetylindoline-2-carboxylic acid wherein N-acetyl-L-indoline-2-carboxylic acid is obtained as a crystalline salt.

A further object of this invention is to provide a resolving agent which gives an optically active N-acetylindoline-2-carboxylic acid in both high yield and high optical purity.

Still another object of this invention is to provide a resolving agent which is not expensive and is readily available on a commercial scale.

Other important object of this invention is to provide an industrial efficient method for preparing an optically active N-acetylindoline-2-carboxylic acid with simple operations.

These and other objects of the invention will become more apparent in the detailed description and examples which follow.

These objects are achieved by using an optically active α-amino-ε-caprolactam as the resolving agent for N-acetylindoline-2-carboxylic acid. Additionally, these objects are achieved by the method for preparing an optically active N-acetylindoline-2-carboxylic acid which comprises optically resolving N-acetylindoline-2-carboxylic acid in inert solvent with an optically active α-amino-ε-caprolactam as a resolving agent.

DESCRIPTION OF THE PREFERRED EMBODIMENTS

The resolving agent of this invention is an optically active α-amino-ε-caprolactam and either D- or L- optical isomer thereof can be used. An optically active α-amino-ε-caprolactam is readily prepared by conventional standard methods For example, it is prepared by optical resolution of α-amino-ε-caprolactam with inexpensive optically active carboxylic acids, such as L-2-pyrrolidone-5-carboxylic acid, or by dehydration with ring closure of L-lysine.

N-Acetylindoline-2-carboxylic acid which prepared by any methods can be used for the optical resolution in this invention. For example, it is prepared by N-acetylation of indole-2-carboxylic acid, followed by hydrogenation. Thus, in this invention, it is general to use a chemically synthesized N-acetyl-indoline-2-carboxylic acid. Additionally, in this invention, N-acetylindoline-2-carboxylic acid which includes excess of either L- or D-optical isomer thereof can also be used for the optical resolution.

The optical resolution of N-acetylindoline-2-carboxylic acid is usually carried out by dissolving N-acetylindoline-2-carboxylic acid and D- or L-α-amino-ε-caprolactam in an inert solvent, followed by cooling or concentration.

The inert solvent used in this invention can dissolve α-amino-ε-caprolactam and N-acetylindoline-2-carboxylic acid, and is inert to these compounds and can precipitate the diasteromeric salt. The representative examples of the inert solvent of this invention may be water; lower alkyl alcohols, such as methanol, ethanol or propanol; or these mixtures. Preferably, water or lower alkyl alcohols, more preferably water or ethanol may be used. Especially advantageous inert solvent of this invention is water. When water is used as an inert solvent, the yield and optical purity of the product may be improved, and economically and advantageously optical resolution can be carried out on a commercial scale.

The resolving agent in this invention is used at a ratio of 0.1 to 2.0 moles, preferably 0.5 to 0.9 mole based on one mole of N-acetylindoline-2-carboxylic acid. When N-acetylindoline-2-carboxylic acid which includes excess of either L- or D-optical isomer is resolved, the resolving agent is used at a suitable ratio according to the D/L ratio of N-acetylindoline-2-carboxylic acid.

When water is used as an inert solvent in this invention, the ratio of resolving agent can be decreased. Namely, when the resolving agent is used at a ratio of less than 1.0 mole, preferably 0.5 to 0.9 mole based on one mole of N-acetylindoline-2-carboxylic acid, bases can be used at a suitable ratio, preferably of 0.5 to 0.1 mole. Bases used in this invention can dissolve the N-acetylindoline-2-carboxylic acid which do not form salt with α-amino-ε-caprolactam in water. Representative examples of the base are sodium hydroxide, potassium hydroxide and ammonia. Preferably ammonia may be used.

The reactions of the resolving agent with N-acetylindoline-2-carboxylic acid in this invention are carried out according to the following standard methods. N-acetylindoline-2-carboxylic acid and the resolving agent are separately dissolved in each inert solvent and then both solutions are mixed. As an another method, both compounds are dissolved by turns in the inert solvent. As the other method, the salt which are formed in advance between N-acetylindoline-2-carboxylic acid and the resolving agent is dissolved in the inert solvent.

The resulting solution is cooled or concentrated and diastereomeric salts are separated. This fractional crystallization is run at the temperature between the freezing point and the boiling point of the solvent used, preferably 0° C. to 80° C.

The resulting diastereomeic salts can be converted into the free compounds, by liberating the latter with stronger acids or bases. Thus liberated optically active N-acetylindoline-2-carboxylic acid can be converted into the corresponding optically active indoline-2-carboxylic acid according to conventional methods, e.g., by hydrolyzing with aqueous hydrochloric acid. The resulting L-indoline-2-carboxylic acid can be converted to 1-carboxylalkanoyl-L-indoline-2-carboxylic acid which is antihypertensive agent.

The invention will be more clearly understood with reference to the following Examples.

EXAMPLE 1

20.0 g of N-acetylindoline-2-carboxylic acid and 12.5 g of L-α-amino-ε-caprolactam were dissolved in 136 ml of hot water. A solution was cooled to 45° C. and seeded with 0.01 g of N-acetyl-L-indoline-2-carboxylic acid·L-α-amino-ε-caprolactam salt. The stirred mixture was further cooled to 15° C. over the period of 2 hours and the stirring continued at 15° C. for additional 30 minutes.

The white precipitate was filtered, washed with cold water and dried. The first salt weighed 11.6 g and corresponded to a yield of 35.7% based on N-acetylindoline-2-carboxylic acid. The salt was suspended in 116 ml of 1 N aqueous hydrochloric acid and the resulting precipitate was filtered, washed with water and dried, to yield 6.57 g of N-acetyl-L-indoline-2-carboxylic acid; $[\alpha]_D^{25} = -135.6°$ (c=1 in ethanol).

The mother liquor from the above first crystallization was evaporated to 71.4 g, then seeded at 48° C. with 0.01 g of N-acetyl-L-indoline-2-carboxylic acid·L-α-amino-ε-caprolactam salt.

According to the method of the first crystallization, the second salt was crystallized, filtered, washed and dried. It weighed 3.35 g and corresponded to a yield of 10.3% based on N-acetylindoline-2-carboxylic acid. The salt was suspended in 1 N aqueous hydrochloric acid and filtered to yield 1.90 g of N-acetyl-L-indoline-2-carboxylic acid; $[\alpha]_D^{25} = -135.7°$ (c=1 in ethanol).

The total amount of N-acetyl-L-indoline-2-carboxylic acid was suspended in 50 ml of 2 N aqueous hydrochloric acid, followed by refluxing for 3 hours. It was cooled to room temperature, neutralized with 5% sodium hydroxide solution and filtered, to yield 6.20 g of L-indoline-2-carboxylic acid; $[\alpha]_D^{25} = -116.5°$ (c=1 in 2 N hydrochloric acid).

EXAMPLE 2

To the suspension of 20.0 g of N-acetylindoline-2-carboxylic acid and 6.24 g of L-α-amino-ε-caprolactam in 60 ml of water was added 2.76 g of concentrated ammonium hydroxide solution and warmed until a solution was formed. The solution was cooled to 43° C. and seeded with 0.01 g of N-acetyl-L-indoline-2-carboxylic acid·L-α-amino-ε-caprolactam salt.

It was cooled to 15° C. over a 2 hours period and the stirring continued for additional 30 minutes at 15° C. The precipitated salt was filtered, weighed 9.58 g and corresponded to a yield of 29.5% based on N-acetylindoline-2-carboxylic acid. The first salt was then suspended in 96 ml of 1 N aqueous hydrochloric acid. The precipitate was filtered, washed with water and dried to yield 5.43 g of N-acetyl-L-indoline-2-carboxylic acid; $[\alpha]_D^{25} = -136.1°$ C. (c=1 in ethanol).

The mother liquor from the above first crystallization was evaporated to 47.0 g, then seeded and cooled, according to the method of the first crystallization. The precipitated salt was filtered, washed with cold water and dried. The weight of the second salt was 2.31 g corresponding to a yield of 7.1% based on N-acetylindoline-2-carboxylic acid. It was treated with 1 N aqueous hydrochloric acid to yield 1.31 g of N-acetyl-L-indoline-2-carboxylic acid; $[\alpha]_D^{25} = -134.6°$ (c=1 in ethanol).

The total N-acetyl-L-indoline-2-carboxylic acid weighed 6.74 g was refluxed in 40 ml of 2 N aqueous hydrochloric acid for 3 hours. After cooling to room temperature, a solution was neutralized with 25% sodium hydroxide solution, the resulting precipitate collected, washed with water and dried, to yield 4.93 g of L-indoline-2-carboxylic acid; $[\alpha]_D^{25} = -116.0°$ (c=1 in 2 N hydrochloric acid).

EXAMPLE 3

The mixture of 10.0 g of N-acetylindoline-2-carboxylic acid and 3.12 g of L-α-amino-ε-caprolactam in 320 ml of ethanol was warmed until a clear solution was obtained. After cooling to 50° C., 0.01 g of N-acetyl-L-indoline-2-carboxylic acid·L-α-amino-ε-caprolactam salt was seeded.

The stirred mixture was cooled to 25° C. over the period of 2 hours. The precipitated salt was filtered, washed with cold ethanol and dried. It weighed 4.71 g and corresponded to a yield of 29.0% based on N-acetylindoline-2-carboxylic acid. The salt was suspended in 30 ml of 1 N aqueous hydrochloric acid and then the precipitate was filtered, washed with water and dried, to yield 2.61 g of N-acetyl-L-indoline-2-carboxylic acid; $[\alpha]_D^{25} = -121.9°$ (c=1 in ethanol).

The suspension of the precipitate in 15 ml of 2 N aqueous hydrochloric acid was refluxed for 3 hours. It was cooled to the room temperature and neutralized with 25% sodium hydroxide solution. The crystalline precipitate was filtered, washed with water and dried to yield 2.00 g of L-indoline-2-carboxylic acid; $[\alpha]_D^{25} = -94.4°$ (c=1 in 2 N hydrochloric acid).

EXAMPLE 4

10.0 g of N-acetylindoline-2-carboxylic acid and 6.25 g of L-α-amino-ε-caprolactam were dissolved in 700 ml of hot ethanol. After cooling to 50° C., 0.01 g of N-acetyl-L-indoline-2-carboxylic acid·L-α-amino-ε-caprolactam salt was seeded. The stirred mixture was cooled to 25° C. over the period of 2 hours. The white precipitate was filtered, washed with cold ethanol and dried. It weighed 7.64 g and corresponded to a yield of 47.0% based on N-acetylindoline-2-carboxylic acid. The salt was suspended in 50 ml of 1 N aqueous hydrochloric acid and the resulting precipitate was filtered, washed and dried to give 4.23 g of N-acetyl-L-indoline-2-carboxylic acid; $[\alpha]_D^{25} = -65.5°$ (c=1 in ethanol).

The suspension of the precipitate in 25 ml of 2 N aqueous hydrochloric acid was refluxed for 3 hours. The solution was cooled to room temperature and neutralized with 25% sodium hydroxide solution, the resulting precipitate filtered, washed with water and dried, to give 3.10 g of L-indoline-2-carboxylic acid; $[\alpha]_D^{25} = -57.3°$ (c=1 in 2 N hydrochloric acid).

EXAMPLE 5

10.0 g of N-acetylindoline-2-carboxylic acid (D:L ratio=33:67) and 4.20 g of L-α-amino-ε-caprolactam were dissolved in 540 ml of hot ethanol. A solution was cooled to 50° C. and seeded with 0.01 g of N-acetyl-L-indoline-2-carboxylic acid·L-α-amino-ε-caprolactam salt. It was cooled to 25° C. over the period of 2 hours and the white precipitated salt was filtered, washed with cold ethanol and dried. The salt wieghed 7.59 g was suspended in 50 ml of 1 N aqueous hydroxhloric acid and the resulting precipitate was filtered, washed with water and dried, to yield 4.20 g of N-acetyl-L-indoline-2-carboxylic acid; $[\alpha]_D^{25} = -130.6°$ (c=1 in ethanol)

The precipitate was suspended in 21 ml of 2 N aqueous hydrochloric acid, followed by refluxing for 3 hours. The solution was cooled to room temperature and neutralized with 25% sodium hydroxide solution, the resulting precipitated crystalline was filtered, washed with water and dried to give 3.07 of L-indoline-2-carboxylic acid; $[\alpha]_D^{25} = -102.8°$ (c=1 in 2 N hydrochloric acid).

What is claimed is:

1. In a method for preparing optically active N-acetylindoline-2-carboxylic acid wherein N-acetylindoline-2-carboxylic acid and an optically active resolving agent provided in the form of an optically active α-amino-ε-caprolactam are dissolved in an inert solvent, and wherein a diastereomeric N-acetylindoline-2-carboxylic acid-resolving agent salt is precipitated from the solution formed therefrom by fractional crystallization and wherein said salts are separated and liberated to optically active free acids by treatment with stronger acids, the improvement wherein said inert solvent is water.

2. In a method for preparing optically active N-acetylindoline-2-carboxylic acid wherein N-acetylindoline-2-carboxylic acid, optically active resolving agent provided in the form of an optically active α-amino-ε-caprolactam and a base are dissolved in an inert solvent, and wherein a diastereomeric N-acetylindoline-2-carboxylic acid-resolving agent salt is precipitated from the solutiion formed therefrom by fractional crystallization and wherein said salts are separated and liberated to optically active free acids by treatment with stronger acids, the improvement wherein said inert solvent is water.

* * * * *

UNITED STATES PATENT AND TRADEMARK OFFICE
CERTIFICATE OF CORRECTION

PATENT NO. : 4,824,964
DATED : April 25, 1989
INVENTOR(S) : Satoru Miyata, Hiromi Fukuda, Shinzo Imamura It is certified that error appears in the above-identified patent and that said Letters Patent is hereby corrected as shown below:

Column 3, line 53, change 5% to 25%.

Signed and Sealed this

Twenty-second Day of May, 1990

*Attest:*

HARRY F. MANBECK, JR.

*Attesting Officer*        *Commissioner of Patents and Trademarks*